United States Patent [19]

Roxburg et al.

[11] Patent Number: 4,527,559

[45] Date of Patent: Jul. 9, 1985

[54] ENDOTRACHEAL TUBE ANCHORING MECHANISM

[76] Inventors: Dwight W. Roxburg, 3050 NE. 89th St., Seattle, Wash. 98115; Linda M. Magnuson, 2357 N. 193rd St., Seattle, Wash. 98133

[21] Appl. No.: 434,774

[22] Filed: Oct. 18, 1982

[51] Int. Cl.³ ............................................. A61M 16/00
[52] U.S. Cl. ...................... 128/207.17; 128/DIG. 26; 128/136; 604/174
[58] Field of Search ...................... 128/200.26, 207.14, 128/207.15, 207.16, 207.17, 207.18, DIG. 26, 136, 132 R, 12, 787, 152, 360, 359; 433/140; 604/174

[56] References Cited

U.S. PATENT DOCUMENTS

| | | | |
|---|---|---|---|
| 190,908 | 5/1877 | Rogers | 128/360 |
| 721,185 | 2/1903 | Heckard | 128/207.14 |
| 2,573,923 | 11/1951 | Mezz | 128/152 |
| 2,694,397 | 11/1954 | Herms | 128/136 |
| 2,954,030 | 9/1960 | Jozwiak | 128/360 |
| 3,022,915 | 2/1962 | Mullin | 128/360 |
| 3,176,690 | 4/1965 | H'Doubler | 128/DIG. 26 |
| 3,568,680 | 3/1971 | Raimo | 128/207.14 |
| 3,602,227 | 8/1971 | Andrew | 128/207.17 |
| 3,648,703 | 3/1972 | Manker | 128/DIG. 26 |
| 3,713,448 | 1/1973 | Arrott | 128/207.17 |
| 3,768,465 | 10/1973 | Helmer | 128/136 |
| 3,794,026 | 2/1974 | Jacobs | 128/207.15 |
| 3,927,676 | 12/1975 | Schultz | 128/207.17 |
| 3,946,742 | 3/1976 | Eross | 128/207.17 |
| 3,971,370 | 7/1976 | Halford et al. | 128/136 |
| 3,973,569 | 8/1976 | Sheridan et al. | 128/207.17 |
| 3,987,798 | 10/1976 | McGinnis | 128/207.17 |
| 4,156,428 | 5/1979 | Henkin | 128/207.15 |
| 4,166,467 | 9/1979 | Abramson | 128/207.14 |
| 4,167,946 | 9/1979 | Sandstrom | 128/207.17 |
| 4,235,229 | 11/1980 | Ranford et al. | 128/207.17 |
| 4,249,529 | 2/1981 | Nestor et al. | 128/207.17 |
| 4,270,529 | 6/1981 | Muto | 128/207.17 |

FOREIGN PATENT DOCUMENTS

| | | | |
|---|---|---|---|
| 2336571 | 2/1974 | Fed. Rep. of Germany | 604/174 |
| 510754 | 8/1939 | United Kingdom | 128/359 |

OTHER PUBLICATIONS

Martinez, "An Improved Cuffed Tracheostomy Tube for Use with Intermittent Positive Pressure Breathing", Journal of Thoracic & Cardiac Surgery, vol. 47, No. 3, Mar. 1964, pp. 404–405.

*Primary Examiner*—Henry J. Recla
*Attorney, Agent, or Firm*—Seidel, Gonda & Goldhammer

[57] ABSTRACT

An endotracheal tube is provided with a plurality of longitudinally spaced transverse apertures along its outer end portion. The apertures are formed by securing a latex rubber strip to the outer surface of the tube at spaced locations or the apertures are formed in a longitudinal ridge of a tube having an oval cross section. After the tube is inserted into the trachea, bodily shifting of the tube is deterred by threading a twill tape through the aperture of a tracheostomy tube next to the tracheostomy incision or the aperture of an oral endotracheal tube next to the mouth of the patient and tying the ends of the tape behind the neck of the patient. If the tube is inserted through the oral cavity, an elongated bite block having a longitudinal reentrant side may be secured to the tube with the twill tape by threading the twill tape through an aperture in the tube, wrapping it around the tube and bite block with the reentrant side engaging the tube, threading the tape through an aperture in the bite block, and tying the bite block to the tube before tying the tape behind the patient's neck.

18 Claims, 18 Drawing Figures

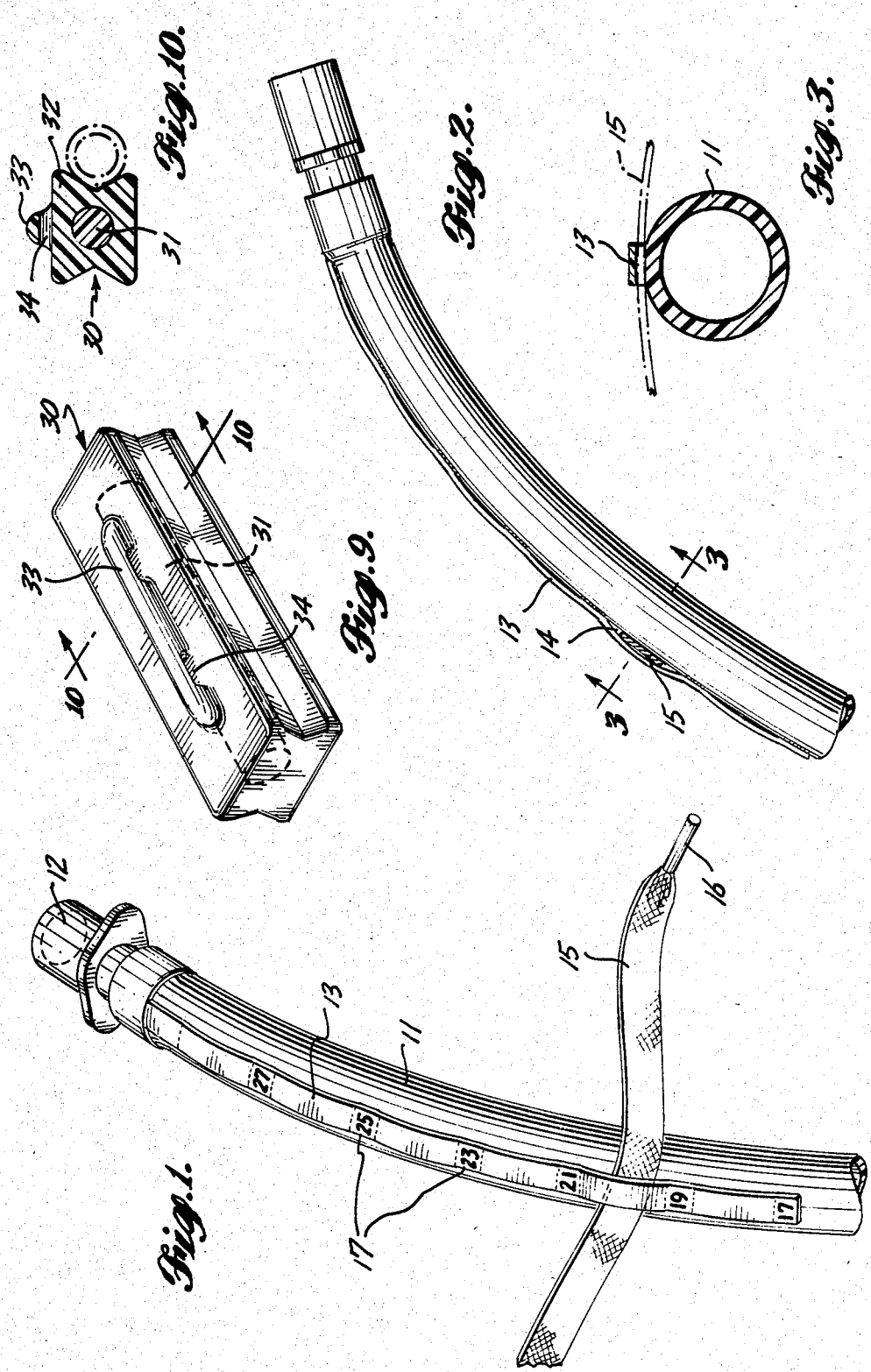

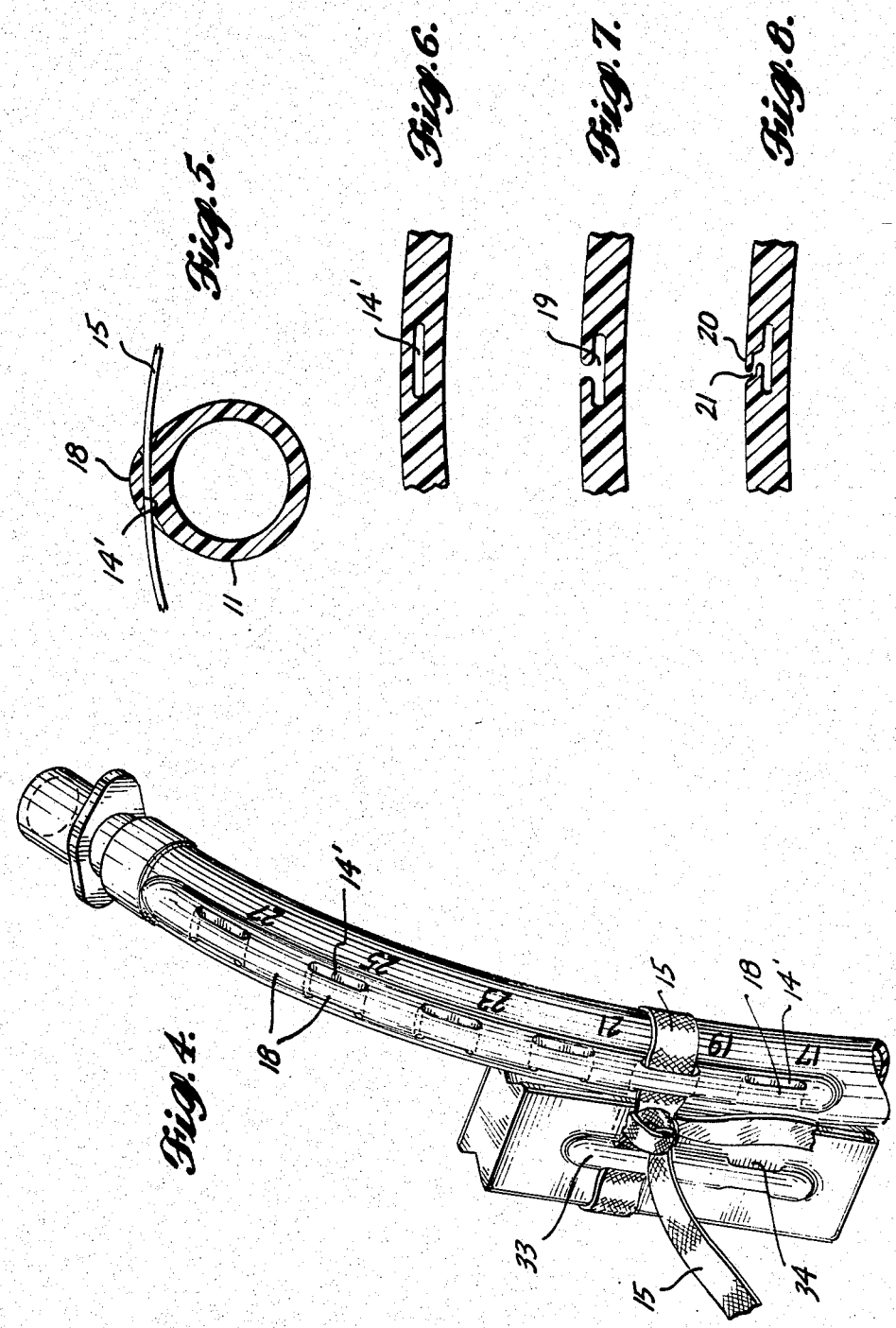

ENDOTRACHEAL TUBE ANCHORING MECHANISM

BACKGROUND OF THE INVENTION

1. Field of the Invention

The present invention relates to endotracheal tubes and, more particularly, to an attachment means for anchoring endotracheal tubes. The attachment means includes discrete locations along the proximal or upper portion of the endotracheal tube to which an attachment strap may be secured so that the tube may be anchored to a patient with the desired length of the tube inserted into the trachea and which deters bodily shifting of the tube within the trachea. The attachment means may be incorporated into the various types of endotracheal tubes as well as bite blocks.

2. Prior Art

Endotracheal tubes are intubated, i.e. inserted into the trachea, to provide a clear passage for air to the lungs if the trachea has been crushed in an automobile accident, for example. Also, a tube may be intubated prior to anesthetizing a patient with a general anesthetic to maintain a clear air passage in case the trachea collapses due to relaxation of the muscles supporting the trachea.

Endotracheal tubes may be intubated through the mouth, designated an oral endotracheal tube; through the nose, designated a nasal endotracheal tube; or through a tracheostomy incision in the front of the neck and trachea, designated a tracheostomy tube. In an emergency situation an oral endotracheal tube is normally used to provide an air passage to the lungs. After the patient's condition has been stabilized, which may require a week or more, the oral endotracheal tube is removed, a tracheostomy incision is made in the neck and trachea, and a tracheostomy tube is intubated through the tracheostomy incision to provide the air passage. Since bacteria grow rapidly within the lumen or passage of the tube, both oral endotracheal tubes and tracheostomy tubes are replaced daily with new sterile tubes.

The tubes also may include an inflatable endotracheal balloon or cuff which surrounds and is fixed to the outer surface of the tube adjacent to its lower end. After the tube is inserted into the trachea, the bulb-shaped cuff is inflated with air through a small diameter tube connected to the cuff interior and which runs upward along the tube to the external portion of the tube. The inflated cuff seals the space between the endotracheal tube and tracheal wall, preventing air from escaping from the lungs past the exterior of the tube and preventing saliva and other liquids from draining into the lungs.

The trachea can be stretched and permanently deformed if the cuff is overinflated. Therefore, as the cuff is inflated, passage of air past the cuff is monitored using a stethoscope. When passage of air ceases inflation of the cuff is stopped. The pressure exerted by the cuff against the tracheal wall is sufficient to prevent passage of air past the cuff but not sufficient to prevent movement between the cuff and the tracheal wall.

Since the trachea in children is not as pliable as in an adult, an inflated cuff could more easily stretch and permanently deform the trachea of a child. Therefore pediatric endotracheal tubes do not include inflatable cuffs and the space between the tube and the trachea must be suctioned frequently to deter saliva from collecting in the lungs.

To insure that the tube is not inserted so far that the lower end is within one of the main stem bronchi causing one of the lungs not to inflate, bilateral chest excursion, i.e. movement of both sides of the chest during breathing, is observed. To verify the location of the lower end of the tube within the trachea, an X-ray opaque color strip may be incorporated along the length of the tube. After the tube is inserted into the lumen of the trachea, the cuff is inflated, the tube is anchored in place and proper positioning of the tube is verified by X-ray photography.

The length of the endotracheal portion of the tube, i.e. the amount of tube which is inserted into the patient's trachea, is dependent on the length of the patient's trachea and, in the case of a tracheostomy tube, the location of the tracheostomy incision. The tube should be intubated to the proper depth, namely past the tracheal blockage in the case of a crushed trachea and preferably until the lower or distal end of the tube is within a few centimeters of the bronchial bifurcation of the trachea, i.e. just above the right and left main stem bronchi, whether there is a tracheal blockage or the patient is to be anesthetized. The length of the tube projecting outward from the mouth or neck incision of the patient is dependent on the length of the endotracheal portion.

Once the endotracheal tube, whether an oral tube or a tracheostomy tube, has been intubated to the proper depth, it must be anchored to the patient to prevent accidental withdrawal of the tube causing possible asphyxiation due to collapse of the trachea and to prevent further insertion of the tube past the bronchial bifurcation. Since the trachea lengthens and contracts as the patient breathes, there will always be some relative movement between the endotracheal tube cuff and the trachea. Such movement causes scar tissue to form which thickens the wall of the trachea. By anchoring the exterior portion of the tube stationarily such movement is minimized.

Since the tubes are made of pliant material and a comatose patient may bite down on an oral endotracheal tube so that the lumen or passage through the tube is constricted, a bite block may be inserted between the upper and lower teeth of the patient when an oral endotracheal tube is used. The bite block consists of a relatively hard material which either surrounds the tube or has a thickness approximately equal to the diameter of the tube.

Sheridan et al. U.S. Pat. No. 3,973,569 discloses a tracheostomy tube assembly which comprises a tube having a flexible, transversely elongated, fixed flange at the proximal or upper end of the tube; a flexible transversely elongated, slidable flange between the fixed flange and the patient's neck; and a plurality of detachable split rings positioned between the two flanges. As shown in FIG. 3, the assembly is anchored to the patient's neck by a strap inserted through slots in the outer ends of the fixed and slidable flanges with the slidable flange abutting the patient's neck. By inserting a greater number of split rings between the two flanges, the portion of the tube extending out away from the patient's neck is increased and the endotracheal portion is shortened. The Sheridan et al. assembly is objectionable because it is complex comprising numerous parts and the range of tube penetration which may be selected is limited to about 3 centimeters.

The tracheostomy tube retainer disclosed in the McGinnis U.S. Pat. No. 3,987,798 surrounds the upper end of the tube and is banded to the patient's neck by a strap extending through slots in the retainer. The retainer includes a pair of opposed struts which project outwardly perpendicular to the patient's neck and have a plurality of slots spaced longitudinally along the struts. The upper or external end of the tube has a pair of opposed lateral tabs which project transversely outward from the tube. Each tab is inserted into a slot in one of the struts to secure the tube to the retainer. The penetration of the McGinnis's tracheostomy tube is established by inserting the tabs into the desired slots in the retainer struts. The McGinnis assembly has an undesirably large number of interacting parts. Further the retainer permits only about a 4 cm variation in the endotracheal length and the retainer struts project some 5 cm outwardly from the patient's neck.

The tracheostomy tube assembly of the Ranford et al. U.S. Pat. No. 4,235,229 includes a tracheostomy tube and a neck collar which has an outstanding deformable sleeve. The collar is strapped around the patient's neck with a tie. The outer end portion of the tube, which has a plurality of ribs, protrudes through the outstanding collar sleeve. A pair of lugs on the outer end of the sleeve projects transversely inwardly and engages the tube between the ribs to anchor the tube. The range of endotracheal length is limited to about 2.5 cm.

Eross U.S. Pat. No. 3,946,742 discloses a bite block secured to an oral endotracheal tube by wrapping an elastic strap which is secured to the bite block around the endotracheal tube and engaging a selected hole in the strap with a post on the bite block. An attachment strap, permanently secured to the bite block, is wrapped around the neck and secured to a post on the bite block. The tube is not anchored reliably because the strap around the tube may slip, particularly if it is moistened by saliva, allowing the longitudinal position of the tube within the trachea to change.

The clamps disclosed in Andrew U.S. Pat. No. 3,602,227 and Nestor et al. U.S. Pat. No. 4,249,529 encircle and grip an endotracheal tube. Such clamps are strapped around the neck and/or head of the patient with attachment straps. Since the tube is made of flexible material which becomes slippery when moistened, it may slip relative to the clamp.

In the Schultz U.S. Pat. No. 3,927,676 and Arrott U.S. Pat. No. 3,713,448, oral endotracheal tubes are held with adhesive tape. However, in replacing the tubes at least daily, repeated stripping of adhesive tape skins the patient's face. Also the adhesive, when in contact with saliva, promotes the growth of bacteria which increases the risk of infection.

In summary, the tracheostomy tube attachment mechanisms of the prior art are complex, having numerous parts, and the range of selectable endotracheal length is too limited. The attachment mechanisms of the prior art oral endotracheal tubes have not reliably anchored the tube to the patient.

SUMMARY OF THE INVENTION

It is an object of the present invention to provide an endotracheal tube which, after being inserted into the trachea to the desired location, can be anchored reliably with an attachment strap so that bodily shifting of the tube within the trachea is deterred.

A further object is to provide a plurality of simple and effective anchoring means spaced longitudinally along such an endotracheal tube.

The foregoing objects can be accomplished by an endotracheal tube having transverse slots spaced along its upper end portion. After the tube is inserted into the trachea, it is anchored by threading a twill tape through the slot in a tracheostomy tube adjacent to the tracheostomy incision or through the slot in an oral endotracheal tube adjacent to the mouth of the patient and securing the twill tape around the neck or head of the patient.

It is also an object to provide a bite block which may be secured to such an oral endotracheal tube at discrete predetermined locations along such tube. Such object can be accomplished by an elongated bite block having a longitudinal reentrant, preferably V-shaped, side engageable with an oral endotracheal tube and a slot extending transversely of the bite block length, through which the anchoring strap can be threaded to tie the bite block to the tube.

BRIEF DESCRIPTION OF THE DRAWINGS

FIG. 1 is a top perspective of an oral endotracheal tube and anchoring mechanism in accordance with the present invention, parts being broken away.

FIG. 2 is a side elevation of the FIG. 1 endotracheal tube assembly shown partly in section and having parts being broken away.

FIG. 3 is an enlarged transverse section taken on line 3—3 of FIG. 2, parts being shown in phantom.

FIG. 4 is a top perspective similar to FIG. 1, showing a modified form of the assembly.

FIG. 5 is an enlarged transverse section of the FIG. 4 endotracheal tube assembly.

FIG. 6 is an enlarged longitudinal section of the FIG. 4 endotracheal tube assembly, parts being broken away.

FIG. 7 is an enlarged longitudinal section similar to FIG. 6, showing another embodiment.

FIG. 8 is another enlarged longitudinal section similar to FIG. 6, showing yet another embodiment.

FIG. 9 is a top perspective of one component of the assembly shown in FIG. 4.

FIG. 10 is a transverse section taken on line 10—10 of FIG. 9, an endotracheal tube being shown in phantom.

DETAILED DESCRIPTION

Figure 11:
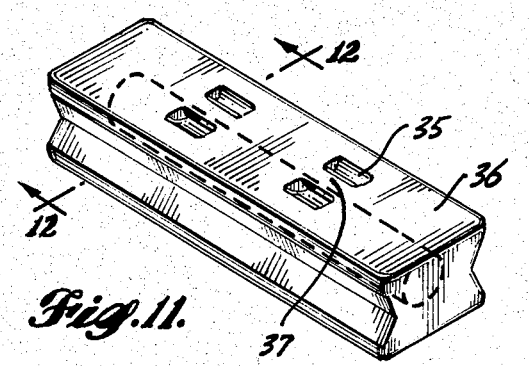
FIG. 11 is a top perspective similar to FIG. 9, showing a second embodiment of the component.

Referring to FIG. 1, the endotracheal tube assembly of the present invention may include an oral endotracheal tube 11 of flexible, bendable polyvinyl chloride plastic which is curved to conform generally to the shape of the oral cavity and trachea. Alternatively the tube may be a nasal endotracheal tube shaped to conform to the nasal cavity and trachea, or a tracheostomy tube shaped to conform to the trachea and project out of the tracheostomy incision. The general shape of all three of the tubes and the lower portion of each tube is conventional.

To enable intubation into the trachea of different sized patients, endotracheal tubes are made in different sizes with inside diameters or lumens graduated in 0.5 millimeter increments from 2 millimeters to 5.5 millimeters for pediatric use and 6 millimeters to 11 millimeters for adults. A standard adapter 12, shown in FIG. 1, to which gas supply equipment may be connected is press fitted into the proximal or upper end of the tube. The projecting portion of the adapter is somewhat larger in diameter than the tube. If it is obvious that the endotracheal tube is of such length that the exocorporeal portion of the intubated tube, i.e. the external portion of the tube, will project excessively, the adapter may be removed from the end of the tube, a length of the upper end portion of the tube cut off, and the adapter replaced.

An oral endotracheal tube of the present invention is anchored by securing an elongated flexible strip to an anchoring means such as threading a twill tape through an aperture in the tube, next to the patient's mouth and tying the tape firmly around the patient's neck so that the twill tape adjacent to such aperture is pressed against the corners of the patient's mouth. As shown in FIG. 1, a latex rubber strip 13 is attached along the exterior upper end portion of the endotracheal tube 11 with its length extending longitudinally of the tube. The latex strip is surgical material which may be 5 to 10 mm wide and about 1.5 mm in thickness. It is attached to the tube over a longitudinal portion of the tube a multiplicity of times the diameter of the tube, such as 8 to 15 times the diameter of the tube and preferably about 12 cm.

As best shown in FIG. 2, longitudinally spaced 5 mm long portions of the latex strip are adhesively bonded to the tube every 2 centimeters forming a row of 4 to 12 apertures in the form of slots 14 each approximately 15 mm long between the strip and tube. Any selected slot will receive a ½-inch (12.7 mm) wide twill tape 15 of woven cloth which is threaded through the slot of a tracheostomy tube nearest the tracheostomy incision or the slot of an oral endotracheal tube nearest the mouth of the patient when the tube has been inserted into the trachea the desired amount. To facilitate such threading, the ends of the twill tape may be bound or wrapped to form a cylindrical end portion as shown at 16 in FIG. 1 or starched flat. Such slot arrangement will permit 2-centimeter incremental positioning of the tube. Since the lower end of the tube should be within only a few centimeters of the bronchial bifurcation, such spacing is adequate. For pediatric use, however, it may be desirable to secure the latex rubber strip every 1 centimeter.

Since the latex rubber strip 13 is soft and pliable, easily sterilized, and compatible with internal use, the tube may be intubated to the extent that the latex rubber strip is within the oral cavity when incorporated into an oral endotracheal tube or within the trachea when incorporated into a tracheostomy tube without causing undue discomfort to the patient or injury to the oral cavity or trachea. If the length of the strip is at least 10 centimeters, the range of length of the present tube which may be inserted into the trachea is far superior to the range of selectable endotracheal length of the positively secured tubes of the prior art. Therefore, tubes of the same length can be used to intubate patients whose size extends over a greater range.

To aid in locating the tube to the proper depth within the trachea by showing how much tube has been inserted and to permit recording of the tube position after it is intubated so that a new identical tube can be intubated to the same depth when the old tube is replaced, the distance between the lower end of the tube and each point of attachment of the latex rubber strip to the tube may be indicated on the tube exterior adjacent to the latex rubber strip or, as shown at 17 in FIG. 1, the numerals may be printed on the latex rubber strip at the points of attachment to indicate the distance to the lower end of the tube in centimeters.

In the second embodiment shown in FIGS. 4 and 5, the slots 14' are formed in an integral ridge 18 extending longitudinally of the upper portion of the endotracheal tube. The slots are formed transversely of the tube ridge as the ridged tube is injection molded. As best shown in FIG. 5, the slotted portion of the tube may be oval in cross section with a passage of circular cross section. However, the tube may have an oval bore and a uniform wall thickness.

As in the first embodiment, the twill tape is threaded through the slot in the tube wall and is tied around the patient's neck or head. The distance between the lower end of the tube and each slot is indicated on the tube in centimeters. If the tube is intubated to the extent that the lowermost slots are within the oral cavity or trachea, the slots will not increase discomfort or injure the oral cavity or trachea. This is contrary to the prior art in which the tracheostomy tube attachment means must always remain outside the body, thereby limiting the degree of choice of endotracheal length of the prior art tube.

The apertures of the second embodiment may be grooves so that the twill tape can be inserted into the groove transversely of its length at the desired location along the tape instead of being threaded through a slot. The inverted T-shaped slot or double undercut slot shown in FIG. 7 at 19 has its crossbar spaced from the outer surface of the tube. The foot of the inverted T upright passage may be closed with a flap 20 having its root integral with the tube wall as shown in FIG. 8 so that inadvertant removal of the twill tape from the groove is deterred. The free end portion of the flap 20 may fold into a notch 21 cut in the surface portion of the tube opposite the flap attachment to provide a flush surface.

Bite blocks prevent the orally intubated patient from collapsing the pliable endotracheal tube by biting it. Previously, as disclosed in the Eross Pat. No. 3,946,742, one tie, which was permanently secured to the bite block, strapped the bite block around the neck of the patient and a second tie, also permanently secured to the bite block, strapped the tube to the bite block. In the present endotracheal assembly, the twill tape may be threaded through a slot in the bite block and tied to the tube before the same tape is fastened around the neck of the patient. Since the twill tape is not permanently secured to the bite block, if the twill tape becomes soiled it may be replaced without replacing the bite block.

As shown in FIG. 9, the bite block is a generally rectangular block typically having a width somewhat greater than its thickness and a length a plurality of times its thickness. The length may be 3 centimeters to 9 centimeters, the width 1 centimeter to 3 centimeters and the thickness 1 centimeter to 2.5 centimeters. Preferably the length is about 7 centimeters, the width between 1.8 centimeters and 2.4 centimeters and the thickness between 1.6 centimeters and 2 centimeters. The length is chosen to permit the bite block to be tied to the oral endotracheal tube next to the patient's mouth and extend into the oral cavity between the patient's upper and lower jaw molars. The thickness of the bite block is greater than the diameter of the endotracheal tube without being so thick as to make it uncomfortable to maintain the bite block between the jaws. The width of the bite block is chosen so that there is an adequate surface on which to bite without making the bite block so large that the bite block and endotracheal tube cannot be inserted comfortably into the oral cavity.

As clearly shown in FIGS. 9 and 10, the bite block 30 includes an elongated cylindrical core 31 of hard plastic material encapsulated longitudinally within the outer layer 32 of pliable material such as polyvinyl chloride. The diameter of the hard plastic core should be approximately the same as the tube passage. Since the most common sizes of oral endotracheal tubes have lumens 7.5 millimeters and 8 millimeters in diameter, preferably the diameter of the inner core 31 is 7.5 millimeters.

Referring to FIGS. 9 and 10, the bite block has at least one longitudinal side which is reentrant over the length of the bite block, such as being concave complemental to the outer surface of the endotracheal tube, or preferably V-shaped so that there will be two lines of contact between the bite block and tubes of different size.

In the bite block shown in FIGS. 9 and 10, a ridge 33 generally parallel to the core projects from a major surface adjacent to the reentrant surface. The ridge includes two or more longitudinally spaced transverse slots 34 so that the block may project into the patient's mouth differing amounts or be reversed end for end if the block has two opposed reentrant surfaces. As shown in FIG. 4, the bite block is secured to the tube by threading one end of the twill tape 15 through the tube slot 14' next to the patient's mouth, wrapping the opposite end of the twill tape around the tube and bite block, threading such opposite end of the twill tape through the bite block slot adjacent to the outer end of the bite block, inserting the opposite end of the bite block into the mouth alongside the intubated endotracheal tube, and knotting the twill tape to maintain the tube in engagement with the bite block reentrant surface. The free ends of the twill tape are then wrapped on opposite sides of the patient's neck, the tape cinched tight and the free ends tied behind the neck of the patient to maintain the tube in the desired location.

Figure 12:
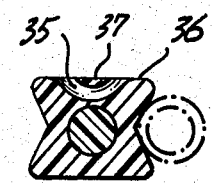
FIG. 12 is a transverse section taken on line 12—12 of FIG. 11, an endotracheal tube being shown in phantom.

FIGS. 11 through 17 show a number of the bite blocks having different apertures through which the twill tape may be threaded to secure the bite block to the endotracheal tube. In the embodiment of FIGS. 11 and 12, two or more longitudinally spaced underpass or tunnel slots 35 are formed in the bite block between the inner core and the flat major surface 36 adjacent to the longitudinal reentrant surface. Both ends of each underpass are in such major surface, creating a bridge 37 parallel to the inner core. The bite block is tied to the tube in a manner similar to the embodiment of FIG. 9.

Figure 14:
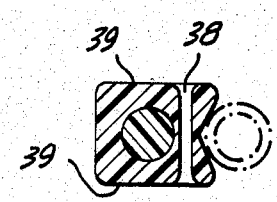
FIG. 14 is a transverse section taken on line 14—14 of FIG. 13, an endotracheal tube being shown in phantom.
Figure 13:
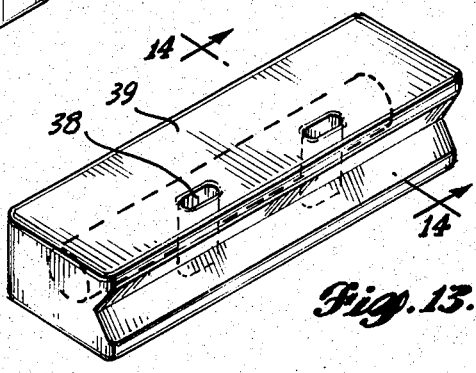
FIG. 13 is another top perspective similar to FIG. 9, showing a third embodiment of the component.

The embodiment of FIGS. 13 and 14 has a plurality of slots 38 penetrating through the block between the inner core and one longitudinal reentrant surface. As best shown in FIG. 14, the slots are generally perpendicular to the flat major surfaces 39 adjacent to the reentrant surface. The bite block is secured to the endotracheal tube with the reentrant surface in contact with the tube by threading the twill tape through one slot in the tube and one bite block slot 38, wrapping the tape around the tube and tying the tape.

Figure 15:
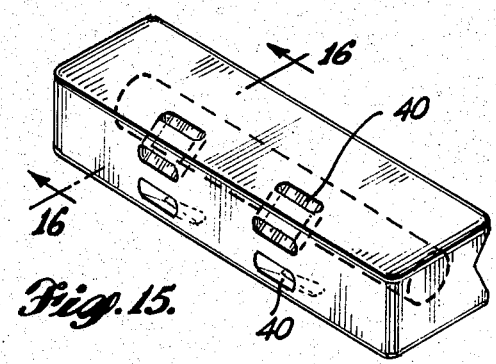
FIG. 15 is another top perspective similar to FIG. 9, showing a fourth embodiment of the component.
Figure 16:
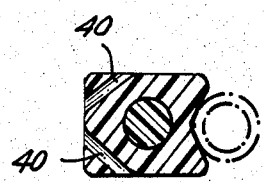
FIG. 16 is a transverse section taken on line 16—16 of FIG. 15, an endotracheal tube being shown in phantom.

The bite block shown in section in FIGS. 15 and 16 includes only one longitudinal reentrant surface. Two apertures 40 subtend the corners of the bite block opposite the reentrant surface. To tie the bite block to the tube the twill tape is threaded in series through one slot from one major surface adjacent to the reentrant surface and threaded through the other slot from the surface opposite the reentrant surface.

Figure 17:
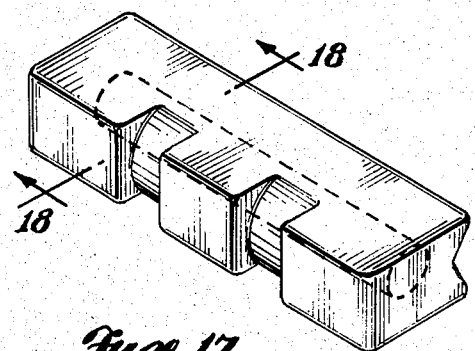
FIG. 17 is yet another top perspective similar to FIG. 9, showing a fifth embodiment of the component.
Figure 18:
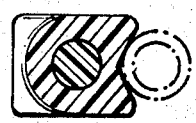
FIG. 18 is a transverse section taken on line 18—18 of FIG. 17, an endotracheal tube being shown in phantom.

The final embodiment shown in FIGS. 17 and 18 is similar to the FIGS. 15 and 16 embodiment except that semicircular grooves in the flat surface opposite the longitudinal reentrant surface are substituted for the apertures. The grooves extend from one major surface adjacent to the reentrant surface to the opposite major surface adjacent to the reentrant surface. The bite block is secured to the endotracheal tube with the reentrant surface against the tube by threading the twill tape through a slot in the tube, wrapping the tape around the bite block with a portion of the tape within one of the bite block grooves and tying the twill tape.

In summary, the disadvantages of the prior art endotracheal tube attachment mechanisms are overcome in the present invention by eliminating the complex tube holders which had to be secured to the tube and incorporating into the tube a plurality of simple anchoring means to which a strap may be directly attached.

We claim:

1. An endotracheal tube comprising an elongated tube having an interior lumen, an exterior surface and a row of preformed apertures spaced longitudinally along and extending transversely of the tube for securing the endotracheal tube to a patient, each aperture being exterior to the lumen and defining a passage having opposite open ends terminating at the exterior surface of the tube, the tube having an exterior ridge extending longitudinally thereof and formed by a lateral portion of the tube wall having increased radial thickness, and wherein said apertures extend transversely through said ridge.

2. The tube defined in claim 1, in which the apertures are inverted T-shaped slots, the crossbars of the T extending substantially parallel to the longitudinal axis of the tube and the leg of the T having an open end terminating at the exterior surface of the tube whereby a twill tape may be inserted into a slot transversely of its length and inadvertent removal of the twill tape is deterred.

3. The tube defined in claim 2, including a flap extending across the foot of an inverted T-shaped slot adjacent the exterior surface of the tube.

4. An endotracheal tube assembly comprising the endotracheal tube defined in claim 1 and an elongated flexible strip removably threaded through a selected one of the apertures.

5. The tube assembly defined in claim 4, in which the flexible strip has a stiffened end portion to enable easy threading of the flexible strip through the selected one of the apertures.

6. The tube assembly defined in claim 4, including an elongated block having a transverse aperture, said bite block being removably secured to the tube by tying said bite block to the tube with the flexible strip.

7. An endotracheal tube comprising an elongated tube having an interior lumen, an exterior surface and a row of preformed apertures spaced longitudinally along and extending transversely of the tube for securing the endotracheal tube to a patient, the tube having an elongated strip extending along the elongated tube, said strip being secured to the exterior surface at locations spaced along the elongated tube, the apertures being defined between the exterior surface of the tube and the strip, said strip having a width substantially greater than its thickness.

8. The tube defined in claim 7, in which the strip is latex rubber.

9. An endotracheal tube assembly comprising an elongated tube, an elongated flexible strip and an elongated bite block, said tube having an interior lumen, an exterior surface and a row of preformed apertures spaced longitudinally along and extending transversely of the tube for securing said tube to a patient, each aperture in said tube being exterior to the lumen and defining a passage having opposite open ends terminating at the exterior surface of said tube, said elongated flexible strip being removably threaded through a selected one of the apertures in said tube, said bite block having a transverse aperture extending therethrough, said bite block being secured to said tube by tying said bite block to said tube with said flexible strip passing through a selected aperture in said tube and said aperture in said bite block.

10. The tube assembly defined in claim 9, in which the bite block includes an elongated hard core encapsulated in a material not as hard as said core, said core being of thickness at least substantially as great as the diameter of the tube lumen.

11. An endotracheal tube comprising an elongated tube having an interior lumen, an exterior surface and a row of preformed apertures spaced longitudinally along and extending transversely of the tube for securing the endotracheal tube to a patient each aperture being exterior to the lumen and defining a passage having opposite open ends, the tube having an exterior ridge extending longitudinally thereof, said ridge having an exterior surface continuous with the exterior surface of the tube, said apertures extending transversely through said ridge with said opposite open ends terminating at the exterior surface of said ridge, said ridge having a width adjacent to the apertures substantially greater than its height.

12. The tube defined in claim 11, in which the ridge is a portion of the tube wall of increased radial thickness.

13. The tube defined in claim 12, in which the ridge has a transverse cross-section which is convex throughout.

14. An endotracheal tube assembly comprising the endotracheal tube defined in claim 26 and an elongated flexible strip removably threaded through a select one of the apertures, said flexible strip having a stiffened end portion to enable easy threading of the flexible strip through the selected one of the apertures.

15. An endotracheal tube assembly comprising the endotracheal tube defined in claim 26, an elongated flexible strip removably threaded through a selected one of the apertures, and an elongated bite block having a transverse aperture, said bite block being removably secured to the tube by tying said bite block to the tube with said flexible strip.

16. An endotracheal tube assembly comprising an elongated tube having an interior lumen, an exterior surface and a row of preformed apertures spaced longitudinally along and extending transversly of said tube, and a twill tape removably threaded through a selected one of the apertures, each aperture exterior to the lumen and defining a passage having opposite open ends terminating at the exterior surface of the tube, said twill tape having a stiffened end portion to enable easy threading of the twill tape through the selected one of the apertures.

17. A bite block for use with an endotracheal tube comprising an elongated hard core encapsulated in a block of material not as hard as said core, said block being generally a rectangular parallelepiped configuration and having an aperture therethrough extending transversely to said core, the aperture defining a passage having opposite open ends terminating at the same surface of the block.

18. A bite block for use with an endotracheal tube comprising an elongated hard core encapsulated in a block of material not as hard as said core, said block being generally a rectangular parallelepiped configuration and having an elongated reentrant side, the longest dimension of the elongated reentrant side being generally parallel to said core and means to secure said block to an endotracheal tube such that said reentrant side is parallel and adjacent to said endotracheal tube.

* * * * *

UNITED STATES PATENT AND TRADEMARK OFFICE
CERTIFICATE OF CORRECTION

PATENT NO. : 4,527,559

DATED : July 9, 1985

INVENTOR(S) : Dwight W. Roxburg et al

It is certified that error appears in the above-identified patent and that said Letters Patent is hereby corrected as shown below:

Column 10, lines 7 and 13, for the claim reference numeral "26", each occurrence, should read --11--.

Signed and Sealed this

Twenty-sixth Day of August 1986

[SEAL]

Attest:

DONALD J. QUIGG

Attesting Officer

Commissioner of Patents and Trademarks